United States Patent
Norrby et al.

(10) Patent No.: US 8,182,088 B2
(45) Date of Patent: *May 22, 2012

(54) SYSTEMS AND METHODS FOR DETERMINING INTRAOCULAR LENS POWER

(75) Inventors: Sverker Norrby, Leek (NL); Rolf Bergman, Uppsala (SE)

(73) Assignee: Abbott Medical Optics Inc., Santa Ana, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 13/021,498

(22) Filed: Feb. 4, 2011

(65) Prior Publication Data

US 2011/0128502 A1   Jun. 2, 2011

Related U.S. Application Data

(63) Continuation of application No. 12/419,230, filed on Apr. 6, 2009, now Pat. No. 7,883,208.

(60) Provisional application No. 61/042,697, filed on Apr. 4, 2008.

(51) Int. Cl.
*G02C 7/02* (2006.01)
*A61F 2/16* (2006.01)

(52) U.S. Cl. ...................................... 351/177; 623/6.11

(58) Field of Classification Search .......... 351/200–246, 351/160 R, 160 H, 161, 162, 176–177; 623/6, 623/11, 6.32, 6.28, 6.11
See application file for complete search history.

(56) References Cited

U.S. PATENT DOCUMENTS

| | | | |
|---|---|---|---|
| 4,710,193 | A | 12/1987 | Volk |
| 5,050,981 | A | 9/1991 | Roffman |
| 5,760,871 | A | 6/1998 | Kosoburd et al. |
| 5,777,719 | A | 7/1998 | Williams et al. |
| 5,968,095 | A | 10/1999 | Norrby |

(Continued)

FOREIGN PATENT DOCUMENTS

JP   9196820 A2   7/1997

(Continued)

OTHER PUBLICATIONS

Hill W.E., "Making Iol Power Calculation More Powerful," Eye World Magazine, 2003, pp. 1-4.

(Continued)

*Primary Examiner* — Mohammed Hasan
(74) *Attorney, Agent, or Firm* — Abbott Medical Optics Inc.

(57) ABSTRACT

A system for providing an intraocular lens includes a processor and a computer readable memory. The computer readable memory is configured to communicate with the processor, the memory having stored therein at least one of: one or more ocular dimensions, and at least one predetermined refractive outcome. The memory further includes a sequence of instructions which, when executed by the processor, cause the processor to select an intraocular lens, select a power of an intraocular lens, or provide an intraocular lens. The sequence of instructions includes determining one or more dimensions of an eye. The instructions also include calculating, based on a mathematical relationship, a distance from an apex of a cornea of the eye to an apex or plane of the intraocular lens after insertion into the eye. The instructions further calculating an optical power of the intraocular lens suitable for providing a predetermined refractive outcome. The mathematical relationship includes an axial length of the eye, an anterior chamber depth of the natural crystalline lens, and a corneal radius of the eye, but is independent of a thickness of the natural crystalline lens.

15 Claims, 2 Drawing Sheets

U.S. PATENT DOCUMENTS

| | | | |
|---|---|---|---|
| 6,050,687 | A | 4/2000 | Bille et al. |
| 6,095,651 | A | 8/2000 | Williams et al. |
| 6,224,211 | B1 | 5/2001 | Gordon |
| 6,338,559 | B1 | 1/2002 | Williams et al. |
| 6,413,276 | B1 | 7/2002 | Werblin |
| 6,499,843 | B1 | 12/2002 | Cox et al. |
| 6,652,098 | B2 | 11/2003 | Suzaki et al. |
| 6,663,240 | B2 | 12/2003 | Patel |
| 6,695,880 | B1 | 2/2004 | Roffman et al. |
| 6,786,603 | B2 | 9/2004 | Altmann |
| 6,808,265 | B2 | 10/2004 | Cox |
| 6,808,266 | B2 | 10/2004 | Youssefi |
| 6,817,714 | B2 | 11/2004 | Altmann |
| 6,830,712 | B1 | 12/2004 | Roffman et al. |
| 6,905,641 | B2 | 6/2005 | Platt et al. |
| 7,322,699 | B2 | 1/2008 | Barth et al. |
| 2003/0128336 | A1 | 7/2003 | Jethmalani et al. |
| 2004/0057014 | A1 | 3/2004 | Altmann |
| 2004/0085515 | A1 | 5/2004 | Roffman et al. |
| 2004/0088050 | A1 | 5/2004 | Norrby et al. |
| 2004/0100619 | A1 | 5/2004 | Olivier et al. |
| 2004/0119174 | A1 | 6/2004 | Hofmann et al. |
| 2004/0156013 | A1 | 8/2004 | Lindacher et al. |
| 2004/0246440 | A1 | 12/2004 | Andino et al. |
| 2005/0007551 | A1 | 1/2005 | Wakil et al. |
| 2005/0056953 | A1 | 3/2005 | Hofmann et al. |
| 2005/0074616 | A1 | 4/2005 | Harchanko et al. |
| 2005/0104240 | A1 | 5/2005 | Jethmalani et al. |
| 2005/0105048 | A1 | 5/2005 | Warden et al. |
| 2005/0122472 | A1 | 6/2005 | Fisher et al. |
| 2005/0195361 | A1 | 9/2005 | Jethmalani et al. |
| 2005/0200809 | A1 | 9/2005 | Dreher et al. |
| 2006/0238702 | A1 | 10/2006 | Glick et al. |
| 2006/0274268 | A1 | 12/2006 | Andino et al. |
| 2007/0260157 | A1* | 11/2007 | Norrby .................. 600/558 |

FOREIGN PATENT DOCUMENTS

| | | | |
|---|---|---|---|
| WO | WO02088830 | A1 | 11/2002 |
| WO | WO03022137 | A2 | 3/2003 |
| WO | WO03057022 | A1 | 7/2003 |
| WO | WO03096927 | A2 | 11/2003 |
| WO | WO2004028356 | A1 | 4/2004 |
| WO | WO2004039554 | A2 | 5/2004 |
| WO | WO2004060643 | A1 | 7/2004 |
| WO | WO2004072709 | A1 | 8/2004 |
| WO | WO2004096014 | A2 | 11/2004 |
| WO | WO2006053216 | A2 | 5/2006 |

OTHER PUBLICATIONS

Holladay J.T., et al., "A Three-Part System for Refining Intraocular Lens Power Calculations," Journal of Cataract and Refractive Surgery, 1988, vol. 14 (1), pp. 17-24.

International Search Report for Application No. PCT/IB2009/008074, mailed on Jul. 7, 2010, 6 pages.

Norrby et al., "Reduction of trend errors in power calculation by linear transformation of measured axial lengths," J Cataract Refractive Surgery, pp. 100-105, 2003, vol. 29, July.

Norrby S., et al., "Clinical Application of the Lens Haptic Plane Concept with Transformed Axial Lengths," Journal of Cataract and Refractive Surgery, 2005, vol. 31 (7), pp. 1338-1344.

Norrby S., et al., "Comparison of 2 A-scans," Journal of Cataract and Refractive Surgery, 2003, vol. 29 (1), pp. 95-99, July.

Norrby S., et al., "Sources of Error in Intraocular Power Calculation," Journal of Cataract & Refractive Surgery, 2008, vol. 34 (3), pp. 368-376, July.

Norrby S., "Using the Lens Haptic Plane Concept and Thick-Lens Ray Tracing to Calculate Intraocular Lens Power," Journal of Cataract & Refractive Surgery, 2004, vol. 30 (5), pp. 1000-1005, July.

Norrby, "The Dubbelman eye model analysed by ray tracing through aspheric surfaces," The college eye of Optometrists, pp. 153-161, 2005, vol. 25.

Olsen T., et al., "Intraocular Lens Power Calculation with an Improved Anterior Chamber Depth Prediction Algorithm," Journal of Cataract & Refractive Surgery, 1995, vol. 21 (3), pp. 313-319.

Preussner et al., "Predicting postoperative intraocular lens position and refraction," J. Cataract Refractive Surgery, pp. 2077-2083, 2004, vol. 30.

Savini G., et al., "Intraocular Lens Power Calculation after Myopic Refractive Surgery: Theoretical Comparison of Different Methods," Ophthalmology, 2006, vol. 113 (8), pp. 1271-1282.

Wold S., et al., "The Co linearity Problem in Linear Regression, The Partial Least Squares (PLS) Approach to Generalized Inverses," Society for Industrial and Applied Mathematics Journal on Scientific and Statistical Computing, 1984, vol. 5 (3), pp. 735-743.

* cited by examiner

SYSTEMS AND METHODS FOR DETERMINING INTRAOCULAR LENS POWER

RELATED APPLICATIONS

The present application is a continuation of U.S. Ser. No. 12/419,230 filed on Apr. 6, 2009 now U.S. Pat. No. 7,883,208 B2, which claims priority under 35 U.S.C. §119(e) to provisional application No. 61/042,697, filed on Apr. 4, 2008.

BACKGROUND OF THE INVENTION

1. Field of the Invention

The present invention relates generally to ocular surgical procedures involving implantable or injectable lenses into the eye of a recipient, and more specifically to systems and methods for determination or selection of a lens power for providing emmetropic vision or, if chosen, a specific ametropic vision to a pseudophakic eye.

2. Description of the Related Art

Accurate determination of lens power is an important aspect in providing emmetropia, or a' desired degree of ametropia, to a subject undergoing cataract surgery or other ophthalmic procedures in which the natural crystalline lens is replaced with or supplemented by implantation of an intraocular lens (IOL) into the eye. Measurements of the eye are typically made preoperatively and a lens power is selected based on correlations between the measured values and lens powers providing a desired refractive outcome.

Over the years a number of intraocular lens power calculation formulas have been developed, for example, as discussed in the book published by SLACK Incorporated entitled *Intraocular Lens Power Calculations*, by H. John Shammas, which is herein incorporated by reference in its entirety. These power formulas may be broadly characterized into at least two categories: theoretical formulas, which are based on a geometric optic, two-lens vergence formula; and regression formulas, which are based on regression formulas obtained by fitting data from a large patient database to an equation relating lens power to one or more parameters thought to correlate with lens power. While there has been continued progress in the accuracy of intraocular lens power calculation formulas to obtain better refractive outcomes, undesirable refractive outcomes due to improper intraocular lens power calculations are still relatively common. Apart from the general desire for spectacle-free refractive outcomes, demands for more accurate lens power calculation have also increased due to the introduction of multifocal lenses.

Many of the current formula algorithms were derived by optical back-calculation to agree with the refractive outcome. In this manner they may be confounded with errors in all parameters used in the calculation, and the oversimplification of thin-lens theory. An evaluation of the sources of errors in lens power calculations was recently published by one of the current co-inventors (Sverker Norrby, "Sources of error in intraocular lens power calculation", Journal of Cataract and Refractive Surgery, Vol. 34, pp. 368-376, March 2008, which is herein incorporated by reference in its entirety). In this paper, preoperative estimation of postoperative intraocular lens position was determined to be the largest contributor of error in the refractive outcome of cataract surgery, with an error contribution of 35%, relative to all error sources evaluated.

In most, if not all of the current formula algorithms, there are a number of ocular parameters that are used in deriving an appropriate lens power for implantation into the eye. These parameters include axial length (AL), corneal radius (CR) or power (K), and anterior chamber depth of the natural crystalline lens prior to surgery ($ACD_{pre}$). In general, one or more of these parameters are used to provide the preoperative estimation of postoperative intraocular lens position. The estimated postoperative lens position is then used in combination with one or more of these same parameters to provide an estimate of the correct lens power to provide a desired refractive outcome (typically emmetropia). However, as discussed in the previous paragraph, the use of this term in calculating postoperative lens position is a large error source in this process. In addition, some of these parameters may be unavailable at the time of evaluation. For example, in the case of a patient that has previously received a corneal refractive surgery, such as LASIK or PRK, the original corneal radius or power may no longer be available. It is the corneal radius prior to corneal refractive surgery that is correct to use in the power calculation formulas because they were developed for normal eyes on data pertaining to normal eyes. The corneal refractive surgery has changed the anatomic relations of ocular dimensions. Hence, the CR or K determined for corneas that have had corneal refractive surgery will give erroneous estimates of the IOL position.

Accordingly, better systems and methods are needed that will allow reliable and accurate determination of implanted or injected lens power, and to provide such determination even in cases where knowledge of information such as original corneal radius or power is no longer available.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

The present invention generally provides devices, systems, and methods for selecting ophthalmic lenses and/or an optical power for such lenses that will provide a predetermined refractive outcome. In many cases the desired outcome will be emmetropia, for example, so that the eye into which the lens is located has a visual acuity for distant objects that is at least 20/20 based on a Snellen chart and/or has an Modulation Transfer Function (MTF) that is at least 0.15 or at least 0.20 at a spatial frequency of 50 line pairs per mm. The following disclosure will be primarily directed to embodiments of the invention as they apply to implantable intraocular lenses; however, it will be understood that other embodiments may be applied directly, or indirectly, to other types of ophthalmic lenses including, but not limited to, injectable lenses that may be formed by injection of a polymer fluid or gel into the eye which is subsequently cured or solidified (e.g., using a UV source), corneal implants, corneal surgical procedures such as LASIK or PRK, contact lenses, and other such devices. In some embodiments, various types of ophthalmic devices are combined, for example, an intraocular lens and a LASIK procedure may be used together to provide a predetermined visual outcome. Embodiments of the invention may find particular use with multifocal or accommodating intraocular lenses, where a proper selection of lens power may be particular important for achieving a desired refractive outcome.

Figure 1:
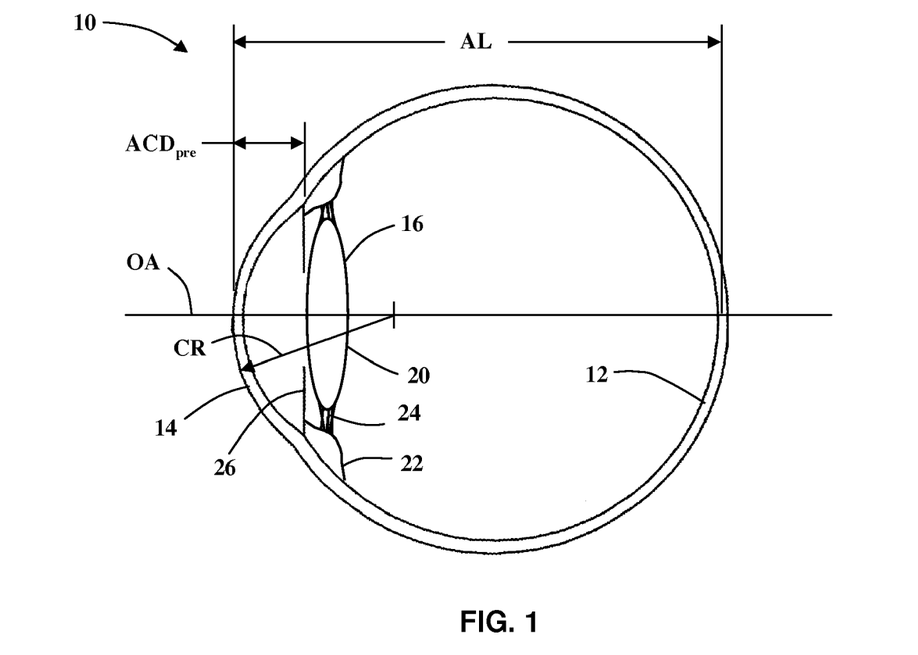
FIG. 1 is a cross-sectional view of a phakic eye containing a natural crystalline lens.

Referring to FIG. 1, which is a cross-sectional view of a phakic eye with the natural crystalline lens, an eye 10 comprises a retina 12 that receives light in the form of an image that is produced by the combination of the optical powers of a cornea 14 and a natural crystalline lens 16, both of which are generally disposed about an optical axis OA. As used herein, an "anterior direction" is in the direction generally toward the cornea 14, while a "posterior direction" is generally in the direction toward the retina 12.

The natural lens 16 is contained within a capsular bag 20, which is a thin membrane that completely encloses the natural lens 16 and is attached to a ciliary muscle 22 via zonules 24. An iris 26, disposed between the cornea 14 and the natural lens 16, provides a variable pupil that dilates under lower lighting conditions (scotopic vision) and constructs under brighter lighting conditions (photopic vision). The ciliary muscle 24, via the zonules 24, controls the shape and position of the natural lens 16, which allows the eye 10 to focus on both distant and near objects. Distant vision is provided when the ciliary muscle 22 is relaxed, wherein the zonules 24 pull the natural lens 16 so that the capsular bag 20 is generally flatter and has a longer focal length (lower optical power). Near vision is provided as the ciliary muscle contracts, thereby relaxing the zonules 24 and allowing the natural lens 16 to return to a more rounded, unstressed state that produces a shorter focal length (higher optical power).

The optical performance of the eye 10 also depends on the spacing between the cornea 14 and the natural lens 16, sometimes referred to as the anterior chamber depth prior to an ocular surgical procedure, $ACD_{pre}$. As used herein, the "anterior chamber depth prior to surgery", "anterior chamber depth prior to an ocular surgical procedure", or "$ACD_{pre}$", is defined as a distance between an apex of a cornea and an apex of a natural crystalline lens of an eye, prior to a surgery to replace the natural crystalline lens 16 with an intraocular lens. In some situations or cases, $ACD_{pre}$ may be defined or approximated as a distance between an apex of a cornea and an anterior surface of the iris 26.

Figure 2:
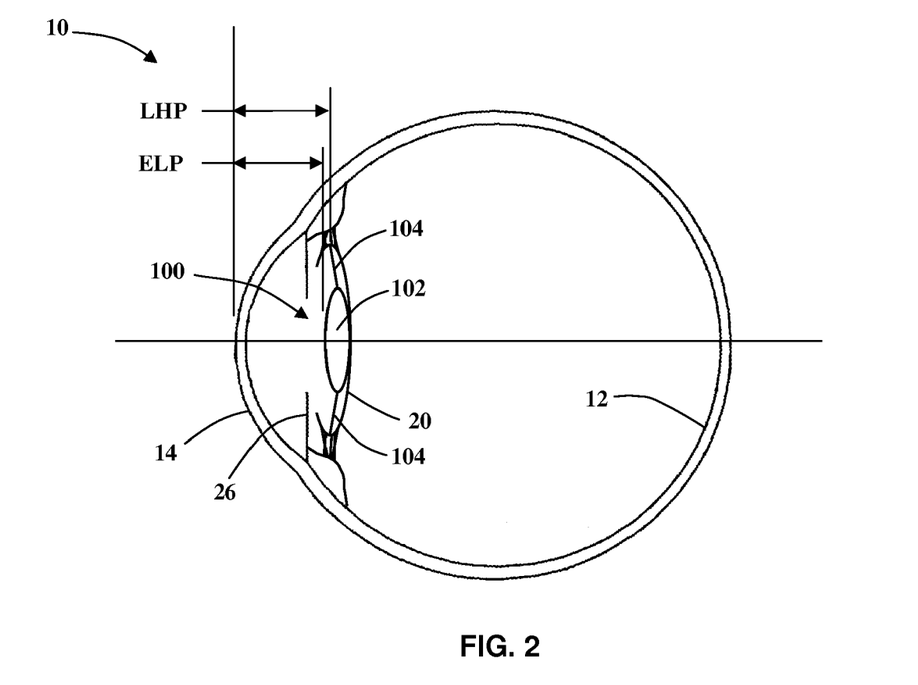
FIG. 2 is a cross-sectional view of a pseudophakic eye containing an intraocular lens.

Referring additionally to FIG. 2, which is a cross-sectional view of a pseudophakic eye 10, the natural crystalline 16 lens has been replaced by an intraocular lens 100 according to an embodiment of the present invention. The intraocular lens 100 comprises an optic 102 and haptics 104, the haptics 104 being generally configured to center the optic 102 within the capsular bag 20. Numerous configurations of haptics 104 relative to optic 102 are well know within the art and embodiments of the present invention may be applied to any of these.

In order to calculate, determine, or estimate the power of an intraocular lens 100 that is able to provide emmetropia or some other predetermined refractive outcome, various dimensions or measurements of the eye 10 are made prior to the surgical procedure. In addition to $ACD_{pre}$, embodiments of the present invention also measure axial length AL of the eye 10, curvature of the cornea CR, is illustrated in FIG. 1.

Various formulations exist within the art that are used for calculation both of lens power and position of an intraocular lens after an ocular surgical procedure. These formulations generally comprise three steps:

1. Measure an eye.
2. Estimate the postoperative position of an intraocular lens.
3. Perform a lens power calculation based on the estimate and/or eye measurements.

The inventors have found that although all three steps are important, the second step of estimating the postoperative position of an intraocular lens may benefit most from improvements in the current state of the measurement arts. For example, in the Norrby reference previously cited in the Background section above, preoperative estimation of postoperative intraocular lens position was determined to be the largest contributor of error in the refractive outcome of cataract surgery, with an error contribution of 35%, relative to all error sources evaluated.

Furthermore, the inventors have found that the combined measurements of AL, $ACD_{pre}$, and CR are highly predictive in calculating the position of the implanted intraocular lens 100 or optic 102. As used herein, a "calculated position" or similar phrases, as applied to an IOL or ophthalmic lens after implantation after an ocular surgical procedure, means an estimated or calculated distance between a cornea of an eye and the IOL or lens after insertion, injection, or formation within the eye. The calculated position will generally be given herein in terms of the "postoperative anterior chamber depth" ($ACD_{post}$), which is defined herein as the distance from an apex of a cornea to an apex of an implanted intraocular lens. The calculated position may also be in terms of an "estimated lens position" (ELP), which is defined as a distance from an apex of a cornea to some effective lens plane of an implanted intraocular lens. For example, J. T. Holladay, M.D. defines ELP as a distance between an apex of a cornea and an effective principal plane of an implantable intraocular lens (e.g., J. T. Holladay, M.D., et al.; J Cataract Refract Surg; January 1988, Vol. 14, pp. 17-24, which is herein incorporated by reference in its entirety). ELP is generally, though not necessarily, greater than $ACD_{post}$.

In certain embodiments, a highly predictive formulation of $ACD_{post}$ is calculated based on the mathematical relationship:

$$ACD_{post} = C1 + (C2 \times AL) + (C3 \times ACD_{pre}) + (C4 \times CR), \quad (1)$$

where AL is an the axial length of the eye, $ACD_{pre}$ is the anterior chamber depth prior to an ocular surgical procedure, CR is a radius of curvature of the cornea, and C1-C4 are constants.

In some embodiments, the calculated position of an IOL or ophthalmic lens after an ocular surgical procedure may be an estimated or calculated distance between the cornea of an eye and a plane passing through the haptics of an ophthalmic lens, referred to herein and a lens haptic plane. One of the co-inventors, Sverker Norrby, has developed a thick-lens calculation scheme based on the lens haptic plane concept. See, for example, Norrby S.; J. Cataract Refractive Surgery 2004; 30:1000-1005; Norrby S, Lydahl E, Koranyi G, J. Cataract Refractive Surgery 2005; 31:1338-1344, U.S. Pat. No. 5,968, 095; and U.S. Patent Application Number 2007-0260157, all of which are herein incorporated by reference in their entirety. The lens haptic plane is defined herein as a plane where the IOL haptic makes contact with the eye tissue. As seen in FIG. 2, the lens haptic plane generally coincides with the equator of the capsular bag 20. As used herein, the distance between the cornea and the lens haptic plane will be designated by "LHP". The LHP may be an additional independent parameter used in calculating or selecting a lens power. It has been observed that the LHP is, in principle, generally independent of the power of an intraocular lens, while $ACD_{post}$ generally depends more on power, although this generally produces only a small shift. The LHP is the plane of contact with tissue (the equator of the capsular bag). Due to angulation of the haptic the anterior surface of an intraocular lens is generally posterior to LHP. The higher the power, the thicker the intraocular lens. Therefore, the higher the lens power, the more anterior is the anterior surface. Thus, the offset between LHP and anterior surface depends on power.

In certain embodiments, a highly predictive formulation for a calculated distance between the cornea and a lens haptic plane of a capsular bag of an eye or of a haptic of an ophthalmic lens has the mathematical relationship:

$$LHP = C1' + (C2' \times AL) + (C3' \times ACD_{pre}) + (C4' \times CR), \quad (2)$$

where AL is the axial length of the eye, $ACD_{pre}$ is the anterior chamber depth prior to an ocular surgical procedure, CR is a radius of curvature of the cornea, and C1'-C4' are constants.

In one embodiment, the coefficients C1-C4 of Equation 1 were calculated based on a linear regression of data presented in Table 1 below. In this embodiment, C1 has a nominal value of 4.236, C2 has a nominal value of 0.08495, C3 has a nominal value of 0.42435, and C4 has a nominal value of −0.3945. Thus, $ACD_{post}$ is given by the equation:

$$ACD_{post} = 4.236 + (0.08495 \cdot AL) + (0.42435 \cdot ACD_{pre}) - (0.3945 \cdot CR) \quad (3)$$

In other embodiments, each of the constants C1-C4 have values that are within plus or minus 20 percent of the nominal value shown in Equation 3, within plus or minus 10 percent of the nominal value, or within plus or minus 5 percent of the nominal value.

In one embodiment, the coefficients C1'-C4' were calculated based on a linear regression of data presented in Table 1 below. In this embodiment, C1' has a nominal value of 4.556, C2' has a nominal value of 0.08495, C3' has a nominal value of 0.42435, and C4' has a nominal value of −0.3945. Thus, LHP is given by the equation:

$$LHP = 4.556 + (0.08495 \cdot AL) + (0.42435 \cdot ACD_{pre}) - (0.3945 \cdot CR) \quad (4)$$

Figure 3:
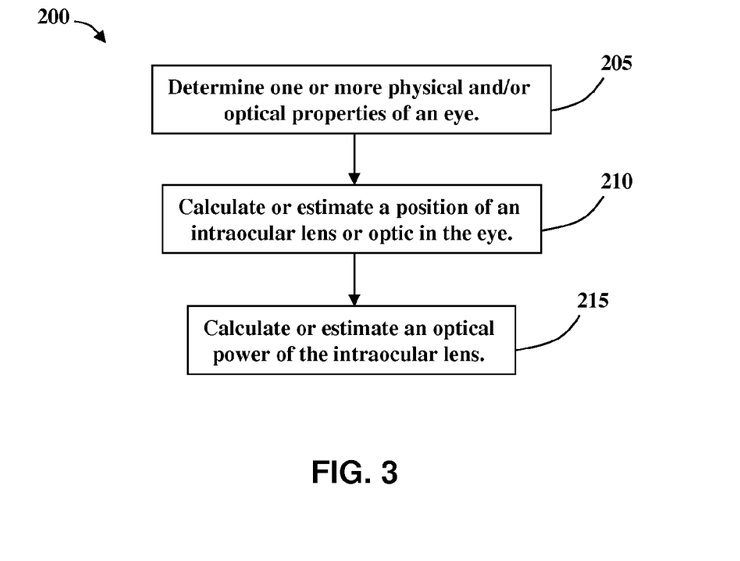
FIG. 3 is a flow chart of a method according to an embodiment of the present invention.

Referring to FIG. 3, in certain embodiments, a method 200 for selecting the intraocular lens 100 or an optical power thereof comprises an element 205 of determining one or more physical and/or optical properties of the eye 100. The method 200 also comprises an element 210 of calculating a position of the intraocular lens 100 or the optic 102 after an ocular surgical procedure. The method 200 additionally comprises an element 215 of calculating or estimating an optical power of the intraocular lens 100 suitable for providing a predetermined refractive outcome.

In the illustrated embodiment shown in FIGS. 1 and 2, element 205 comprises measuring AL, $ACD_{pre}$, and CR of the eye 10. Additionally or alternatively, a corneal power K may be measured or calculated based on CR, K may be expressed in units of Diopters (m$^{-1}$). In such embodiments, a conversion between CR and K is given by the relationship:

$$K = \frac{KI - 1}{CR} \times 1000, \quad (5)$$

where KI, the keratometric index, generally 1.3375. CR and K thus contain the same information. In some embodiments, additional dimensions of the eye may be measured (e.g., natural lens thickness LT, corneal thickness, retinal thickness, or the like). In addition, various physical property of the eye may also be measured or estimated (e.g., a refractive index of a material of the eye, and the like) and/or category information of the patient or IOL (e.g., age, sex, which eye, IOL model, IOL optic and/or haptic dimensions, or the like).

The element 210 of the method 200 comprises calculating a position of the intraocular lens 100 or the optic 102 after an ocular surgical procedure. In the illustrated embodiment of FIGS. 1 and 2, the calculated position of the intraocular lens 100 is based on measured or calculated values of AL, $ACD_{pre}$, and CR of the eye 10. These values may be used in one or more of Equations 1-4 to calculate the lens position. In certain embodiments, the constants C1-C4 or C1'-C4' are selected based on analysis of data for AL, $ACD_{pre}$, and CR using regression routine, for example, based on a multiple linear regression (MLR) analysis or a partial least squares (PLS) regression analysis of data for AL, $ACD_{pre}$, and CR.

In the illustrated embodiment of FIGS. 1 and 2, Equations 1-4 have been found to be highly predictive on $ACD_{post}$ and LHP, for example, having a statistical P-Value of P>0.05, based on a PLS regression analysis of data from Table 1 below. In particular, Equation 2 has been found to have a statistical P-Value of P less than or equal to 0.031. Based on the PLS analysis for this data, Equation 3 has a relatively low statistical variation compared to other prior art formulations in calculating $ACD_{post}$, for example, having Q2 variation of less than or equal to about 0.20, where "about" means±0.01, and a residual standard deviation (RSD) of less than or equal to about 0.3, where "about" means±0.01. It is estimated that these results can improve difference between planned and final outcome, sometimes called mean absolute error (MAE), by 0.07 Diopters to a value of 0.053, based on data from the European cataract outcome study (http://www.eurocat.net, accessed 2008 Jul. 10).

A characteristic of the mathematical relationship described by Equation 2 is that the calculated value of $ACD_{post}$ has a surprisingly low sensitivity to variations in the measured axial length AL. As discussed below in the examples, the sensitivity of Equation 2 is only about 0.45% change in the calculated value of $ACD_{post}$ when the value of AL changes by 1% from a nominal value, for example a nominal value of 24 mm or 25 mm. This is much lower than the sensitivity of other evaluated mathematical relationships based on different prior art combinations of measured eye parameters, which varied from about 0.7% to about 2.4% when the value of AL is changed by 1% from a nominal value. Advantageously, the low dependence on AL of Equations 1-4 allows accurate calculations of $ACD_{post}$ to be made with less accurate measurements of AL.

Another surprising result from the study discussed in the Examples below is that the addition of lens thickness LT to Equations 1-4 showed essentially no correlation of $ACD_{post}$ with LT. This is in contrast to other prior art formulas (e.g., Olsen and Holladay) which include LT along with AL, $ACD_{pre}$, and CR in calculating $ACD_{post}$. Thus, the formulas in Equations 1-4 advantageously determine $ACD_{post}$ and LHP without the need to measure LT at all.

In some embodiments, one or more of the measured variables in Equations 1-4 may be left out; however, this has been found to decrease the predictability. For example, as discussed below in the Examples section, the measurement of CR may be left out and the coefficients for AL and $ACD_{pre}$ be re-evaluated. This can be useful for subjects that have already had a corneal refractive procedure such as LASIK and there is no record of the corneal curvature before the procedure.

The element 210 of the method 200 comprises element 210 of calculating a position of the intraocular lens 100 or the optic 102 after an ocular surgical procedure. Various power calculation formulas are available for this purpose (e.g., Holladay 1, SRK/T, Hoffer Q, and the like). Generally, the lens power calculation only requires preoperative measurements are axial length AL and corneal power K (or equivalently, corneal curvature, CR), and are based on a thin-lens theory approximation for the optical calculation. The following representation is used by Holladay:

$$P_{IOL} = \frac{1336}{AL - ELP} - \frac{1336}{\frac{1336}{\frac{1000}{\frac{1000}{Rfx} - V} + K} - ELP}$$

where AL is the axial length in mm, K is the corneal power in Diopter or $mm^{-1}$, ELP is the estimated postoperative effective lens position in mm, V is the spectacle vertex distance in mm, and IOL is the IOL power in Diopters to obtain Rfx, the desired postoperative spectacle refraction. V is generally not critical and often assumed to be 12 mm.

In the case of emmetropia, the above equation may be reduced to:

$$P_{IOL} = \frac{1336}{AL - ELP} - \frac{1336}{\frac{1336}{K} - ELP}$$

In some embodiments, $ACD_{post}$ may be substituted for ELP in the two equations above.

The method 300 may be incorporated with one or more methods of inserting, injecting, or forming a lens within the individual eyes of the population. Such methods may also comprise making postoperative measurements of the eyes in the population to determine the postoperative position of the lens for each eye within the population and/or to use the information to further refine the mathematical modes defined by Equations 1-4. Additionally or alternatively, such methods may further comprise conducting a statistical analysis of each measured or derived characteristic to determine (1) a correlation between the calculated postoperative lens position and the measured or derived characteristic(s) and/or (2) to determine coefficient value for an equation containing the measured or derived characteristic(s) as variables, the equation configured for calculating a postoperative lens position within an eye.

In certain embodiments, a method of selecting an ophthalmic lens or an optical power thereof comprises determining an axial length and/or other characteristic of an eye having a cornea. The method also comprises calculating a position of an ophthalmic lens after an ocular surgical procedure and calculating an optical power of the ophthalmic lens suitable for providing a predetermined refractive outcome. The calculated position of the ophthalmic lens is based on a mathematical relationship that includes an input parameter representing the axial length of the eye, the mathematical relationship having a sensitivity that is less than or equal to 0.4 percent.

Figure 4:
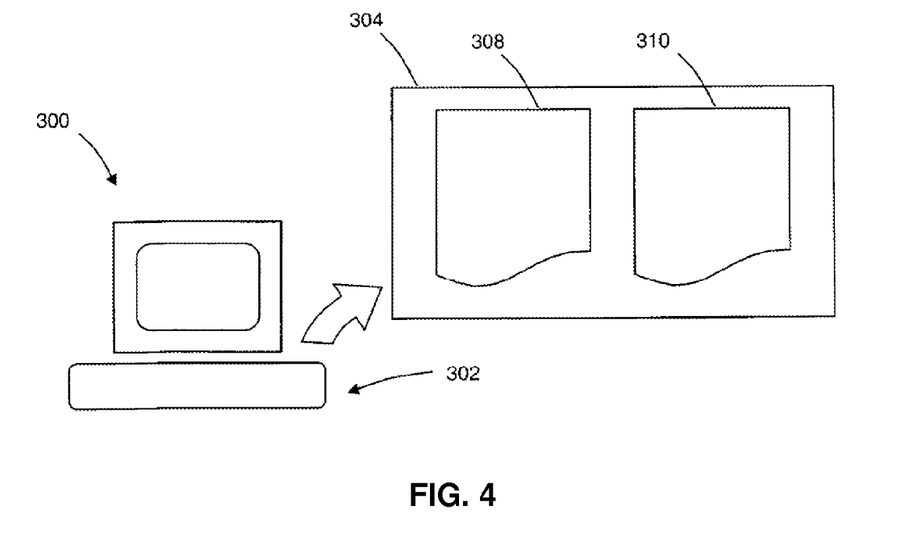
FIG. 4 is a graphical representation of the elements of computing system for selecting an ophthalmic lens according to an embodiment of the present invention.

Referring to FIG. 4, in certain embodiments, a computer system 300 for calculating a postoperative lens position within an eye and/or for selecting an ophthalmic lens or an optical power thereof comprises a processor 302 and a computer readable memory 304 coupled to the processor 302. The computer readable memory 304 has stored therein an array of ordered values 308 and sequences of instructions 310 which, when executed by the processor 302, cause the processor 302 to calculate a postoperative lens position within an eye and/or for selecting an ophthalmic lens or an optical power thereof. The array of ordered values 308 may comprise, for example, one or more ocular dimensions of an eye or plurality of eyes from a database, a desired refractive outcome, parameters of an eye model based on one or more characteristics of at least one eye, and data related to an IOL or set of IOLs such as a power, an aspheric profile, and/or a lens plane. In some embodiments, the sequence of instructions 310 includes determining a location of the lens plane of an IOL, performing one or more calculations to determine a predicted refractive outcome based on an eye model and a ray tracing algorithm, comparing a predicted refractive outcome to a desired refractive outcome, and based on the comparison, repeating the calculation with an IOL having at least one of a different power, a different aspheric profile, and a different lens plane.

The computer system 300 may be a general purpose desktop or laptop computer or may comprise hardware specifically configured performing the desired calculations. In some embodiments, the computer system 300 is configured to be electronically coupled to another device such as a phacoemulsification console or one or more instruments for obtaining measurements of an eye or a plurality of eyes. In other embodiments, the computer system 300 is a handheld device that may be adapted to be electronically coupled to one of the devices just listed. In yet other embodiments, the computer system 300 is, or is part of, refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

Generally, the instructions of the system 300 will include elements of the method 300 and/or parameters and routines for performing calculations of one or more of Equations 1-4.

In certain embodiments, the system 300 includes or is part a phacoemulsification system, laser treatment system, optical diagnostic instrument (e.g., autorefractor, aberrometer, and/or corneal topographer, or the like). For example, the computer readable memory 304 may additionally contain instructions for controlling the handpiece of a phacoemulsification system or similar surgical system. Additionally or alternatively, the computer readable memory 304 may additionally contain instructions for controlling or exchanging data with an autorefractor, aberrometer, and/or corneal topographer, or the like, In some embodiments, the system 300 includes or is part of a refractive planner. The refractive planner may be a system for determining one or more treatment options for a subject based on such parameters as patient age, family history, vision preferences (e.g., near, intermediate, distant vision), activity type/level, past surgical procedures.

EXAMPLES

Various formulas exist in the art for calculating intraocular lens power for an individual subject or patient. In general, these formulations include equations for estimating ELP. Many of these formulas are based on thin-lens theory, in which each lens is reduced to a power at its principal plane. The position of the principal plane may depend on the shape factor of the lens or on the vergence of the incoming light, hence ELP is not generally indicative of the true position of the intraocular lens. The formulas differ from each other in the algorithms for estimation of ELP. These algorithms were obtained by analysis of large amounts of clinical data and adjusted such that the calculated refracted outcome on average agreed with that found postoperatively.

To compensate for deviations in unusually long or unusually short eyes, many formulas also include certain "fudge" factors. For example, the Holladay 1, SRK/T, Hoffer Q formulas include a SF-, A- and ACD-constant, respectively, that is specific for a given intraocular lens model and is associated with an average postoperative position of that model. Manufactures may give preliminary estimates of these constants, which may then be "personalized" by or for a particular surgeon. To "personalize" a constant for a given formula the surgeon may perform several cases with the preliminary constant, and subsequently adjusts the constant such that the mean difference with refractive outcomes becomes zero. Derivation of these formula algorithms is generally based on back-calculation of clinical outcome using thin-lens theory. They may, therefore, be confounded with all errors of the measured parameters involved, and the oversimplification of thin-lens theory.

The Haigis formula is based on thin-lens theory, but has a somewhat different approach. It uses three constants in the algorithm for ELP, two of which are multiplicative coefficients for AL and ACD. By using three constants it can better approximate the nonlinear relationship between AL and ELP. Olsen has presented a formula based on thick-lens theory, though still assuming the paraxial approximation. It uses 5 parameters to predict the postoperative position of the anterior surface of the IOL, $ACD_{post}$ (in mm): AL, ACD, lens thickness (LT in mm), corneal radius (CR in mm), and corneal diameter ("white-to-white" in mm). The advantage with the thick-lens model is that the optical components are represented by the refracting surfaces at their real positions. The challenge is that all input parameters must be correct. There are no "fudge" factors to tweak the results with, except the $ACD_{post}$ prediction algorithm itself. The Holladay 2 formula, which has not been published, resides in the Holladay IOL Consultant software and can use up to 7 parameters in the ELP prediction algorithm: AL, K, ACD, LT, corneal diameter, preoperative refraction in Diopters, and patient age (in years). It is still apparently based on thin-lens theory.

In an effort to evaluate various types of formulas for calculating the position of an implanted intraocular lens, a study was conducted, in which 23 regular cataract patients received either an AMO CeeOn 911A or an AMO TECNIS Z9000 IOL. These lenses have different shapes of the anterior optic surface, but are otherwise identical, and therefore provide the same axial depth in a given eye. Patients were treated in accordance with normal hospital routines; however, additional preoperative and postoperative measurements were performed for the purposes of the study. Zeiss IOLMaster, Zeiss ACMaster (both manufactured by Carl Zeiss Meditec, Inc., Dublin, Calif.). Measurements included axial length, anterior chamber depth, lens thickness and mean corneal radius. Postoperative anterior chamber depth was measured with Zeiss ACMaster. Formulas to estimate postoperative anterior chamber depth in terms of preoperative parameters were analyzed by means of partial least squares regression. The usefulness of fits was judged by the P-value obtained by cross-validation ANOVA.

TABLE 1

Measured eye parameters, implanted intraocular lens, and postoperative refraction for study used to determine. In the "Model" column, C = AMO CeeOn 911A intraocular lens and T = AMO TECNIS Z9000 intraocular lens. Under "Pre-surgery" and "Post-surg.", ".i" and ".o" indicate measurements made using an ACMaster and IOLMaster, respectively.

| | Categories | | | | Pre-surgery measurement | | | | | | Post-surg. Measurement |
|---|---|---|---|---|---|---|---|---|---|---|---|
| Case | Sex | Eye | Model | Age (yrs) | AL.i (mm) | ACD.a (mm) | ACD.i (mm) | CR.i (mm) | LT.a (mm) | WTW.a (mm) | $ACD_{post}$.a (mm) |
| 1 | m | Left | C | 67 | 24.1 | 3.76 | 3.69 | 8.1 | 4.3 | 12.6 | 4.61 |
| 2 | f | Left | C | 78 | 23.52 | 3.56 | 3.52 | 7.8 | 4.64 | 12.9 | 4.65 |
| 4 | m | Right | C | 62 | 24.17 | 3.61 | 3.6 | 7.96 | 4.02 | 11.7 | 4.60 |
| 6 | f | Right | C | 70 | 24.73 | 3.48 | 3.59 | 7.79 | 4.23 | 11.8 | 4.92 |
| 7 | f | Left | C | 75 | 22.98 | 3.64 | 3.43 | 7.64 | 4.11 | 12.8 | 4.39 |
| 8 | f | Right | C | 66 | 23.64 | 3.08 | 3.04 | 7.85 | 4.24 | 10.9 | 4.28 |
| 9 | m | Right | C | 76 | 23.07 | 3.66 | 3.54 | 7.78 | 4.65 | 10.9 | 4.73 |
| 10 | f | Left | C | 76 | 23.13 | 3.7 | 3.23 | 7.67 | 4.51 | 11.2 | 4.30 |
| 11 | f | Right | C | 75 | 23.29 | 3.41 | 3.79 | 7.53 | 4.98 | 11.7 | 4.83 |
| 12 | f | Right | T | 67 | 22.13 | 3.28 | 3.33 | 7.3 | 4.49 | 12.8 | 4.48 |
| 13 | f | Left | T | 77 | 22.34 | 3.75 | 3.23 | 7.49 | 4 | 12.7 | 4.60 |
| 14 | f | Left | T | 67 | 24.32 | 3.26 | 3.21 | 7.95 | 4.68 | 12.9 | 4.29 |
| 15 | f | Left | T | 77 | 22.13 | 2.77 | 2.59 | 7.48 | 4.82 | 12.6 | 4.61 |
| 16 | f | Left | T | 74 | 24.83 | 2.96 | 2.8 | 7.44 | 4.99 | 12 | 4.60 |
| 17 | m | Left | T | 65 | 23.39 | 3.66 | 3.22 | 7.44 | 4.55 | 11.3 | 4.80 |
| 18 | f | Right | T | 64 | 23.2 | 3.08 | 2.79 | 7.79 | 4.98 | 12.4 | 4.24 |
| 19 | f | Left | T | 74 | 23.28 | 3.33 | 3.16 | 7.48 | 4.15 | 12.1 | 4.94 |
| 20 | m | Left | T | 44 | 24.53 | 3.63 | 3.38 | 8.3 | 3.7 | 14 | 4.21 |
| 21 | m | Left | T | 76 | 24.71 | 3.66 | 3.56 | 8.14 | 4.56 | 11.8 | 4.93 |
| 22 | f | Left | T | 69 | 22.31 | 2.91 | 2.85 | 7.99 | 4.25 | 12.5 | 3.98 |
| 23 | f | Left | T | 79 | 22.53 | 2.65 | 2.59 | 7.53 | 4.98 | 13.3 | 4.53 |
| 24 | f | Right | T | 39 | 22.03 | 3.45 | 3.19 | 7.61 | 4.07 | 12.6 | 4.58 |
| | | | Mean: | 69 | 23.21 | 3.38 | 3.24 | 7.73 | 4.45 | 12.3 | 4.52 |
| | | | SD: | 10 | 0.91 | 0.34 | 0.35 | 0.27 | 0.37 | 0.8 | 0.26 |

Of the 23 patients enrolled in the study, 10 received a CeeOn 911A IOL and 13 a Tecnis Z9000 IOL. One patient in the former group did not complete the study, leaving a total of 22 cases for analysis. Data of this type are frequently analyzed by multiple linear regression (MLR); however, such analysis may be valid only if the parameters are not correlated to each other. When the parameters are correlated, partial least squares (PLS) regression is considered a better approach. PLS regression is further capable of handling category variables, such as sex, and can cope with missing data. Accordingly, data in this study was analyzed by PLS regression using SIMCA P 12+ (Umetrics AB, Umeå Sweden). In accordance with the manual of SIMCA, each combination of input parameters is referred to as a "model", not to be confused with IOL model.

For small data sets, as in this study, the prediction power of a model was tested by cross validation by elimination of one observation at a time; thereafter a new model was calculated. This new sub-model was used to predict the observation eliminated. The process was continued until all observations were eliminated once. An average prediction error was then calculated from the sum of squares of all prediction errors of the sub-models. This was used to calculate the statistic $Q^2$, which is an estimate of how much of the variation in the result parameter ($ACD_{post}$ in this case) can be predicted by the model parameters at a chosen level of certainty. A 95% level was chosen for this study. This type of cross validation (CV), also known as "Jack-Knifing", delivers uncertainty intervals for each model variable. CV-ANOVA of the prediction errors yields the residual standard deviation (RSD), and the reliability of the PLS-models as a P-value. As commonly done we consider P<0.05 as statistically significant.

Of the various models evaluated, some of the more relevant ones are reported in Table 2. Some of models shown in Table 2 represent some of the more common measurement combination used in estimating $ACD_{post}$. However, of all the models shown, only model number 8 (which corresponds to embodiments of the present invention discussed in relation to Equations 1-4) proved to be clearly statistically significant (e.g., having a value of P>0.05). This model also had a reasonably low RSD of 0.20.

TABLE 2

Statistical results for various combinations of pre-surgically measured eye dimensions.

| Model No. | Preoperative input variables | Q2 | P | RSD (mm) |
|---|---|---|---|---|
| 4 | Age, AL.i, ACD.a, CR.i, LT.a, WTW.a | 0.055 | 0.582 | 0.22 |
| 5 | Age, AL.i, ACD.a, CR.i, WTW.a | 0.061 | 0.549 | 0.21 |
| 6 | AL.i, ACD.a, CR.i, WTW.a | 0.087 | 0.422 | 0.22 |
| 7 | AL.i, ACD.a, CR.i | 0.230 | 0.083 | 0.21 |
| 8 | AL.i, ACD.i, CR.i | 0.305 | 0.031 | 0.20 |
| 10 | AL.i, ACD.i, CR.i, AL.i·ACD.i, ACD.i·CR.i | 0.417 | 0.182 | 0.15 |
| 12 | AL.i, ACD.i | 0.127 | 0.275 | 0.24 |
| 14 | AL.i, CR.i | 0.011 | 1.000 | 0.23 |
| 16 | AL.i, ACD.i, CR.i, AL.i·ACD.i | 0.467 | 0.083 | 0.16 |
| 17 | AL.i, K.i | 0.011 | 1.000 | 0.23 |
| 26 | AL.i, ACD.a, CR.i, LT.a | 0.228 | 0.086 | 0.20 |

".i" and ".o" indicate measurements made using an ACMaster and IOLMaster, respectively.

For the M8 model, there was a generally strong correlation with $ACD_{pre}$ and CR. Surprisingly, however, there was only a weak correlation with axial length AL. The generally low correlation to AL is surprising, since AL is generally considered as a strong predictor for postoperative intraocular lens position. In present formulas the algorithms for prediction of the postoperative IOL position, or the $ACD_{post}$, were obtained by back-calculation by means of the optical formula. The strong influence AL has on the power calculation itself, probably explains why it then becomes a strong predictor of IOL position.

A sensitivity analysis was also performed for the various terms used in Equations 3 and 4 above, for those found in the currently popular formations discussed above, and for a formula used in U.S. Patent Application Publication Number 2007/0260157 (e.g., the equation shown in paragraph [0061]). To that end, values of the $ACD_{post}$ estimate for each formulation calculated for an average eye model with the following characterization:

AL=24.75 mm
$ACD_{pre}$=3.54 mm
CR=8 mm (or K=42.2 Diopters)

Based on these nominal values, an $ACD_{post}$ calculation was made for each of the formulations cited below in Table 3. Additional $ACD_{post}$ calculations were also made for each formulation in which each of the parameters for each formula was increased by 1 percent above the nominal values above. In this way, a percent change in the calculated $ACD_{post}$ was found for a 1 percent increase in the different parameters used in each formulation. The resulting percent change in the $ACD_{post}$ estimate for the various 1 percent parameter changes is shown in Table 3.

TABLE 3

Calculated sensitivity of the parameters in various formulas for used to estimate $ACD_{post}$.

|  | AL | ACD.pre | CR |
|---|---|---|---|
| Rostock (Eq. (3)) | 0.45 | 0.32 | −0.67 |
| 2007/0260157 publication | 1.20 | −0.75 | −0.75 |
| Holladay | 2.42 | — | −1.49 |
| Haigis | 0.73 | 0.15 | — |
| SRK/T | 0.96 | — | −1.47 |
| Hoffer | 1.25 | — | −0.40 |

The formulation for the 2007/0260157 publication is:

$$LHP=2.486+[0.2174\times(AL+\Delta AL)]-(0.4213\times CR),$$

where $\Delta AL$ is a retinal thickness parameter and is equal to 0.25 mm.

As can be seen from the results in Table 3, the Rostock equation varies only 0.45 percent when the axial length AL parameter is increased by 1 percent from the nominal value. This confirms that the Rostock formulation provides relationships that has a low sensitivity to the value of the axial length AL of the eye. By contrast, the other formulations that were analyzed showed a much higher sensitivity to the value of axial length AL. The least sensitive of these remaining formulations was that of Haigis, which was still more than three times as sensitive as the Rostock equation, Equation 3. These results demonstrate that the Rostock formulation clearly has a very low sensitivity to the value of axial length AL of an eye.

Prediction of postoperative intraocular lens position in cases where a subject has had a previous corneal refractive surgery is an ever increasing problem. The final postoperative position of the intraocular lens is not generally affected by the fact that the patient has had previous corneal surgery. But CR and K have been altered and, therefore, formulas that use either CR or K are no longer valid for these patients where the preoperative values have been lost. In such cases, the Rostock formulation can be adjusted to produce modified Rostock formulas that are independent of CR:

$$ELP=3.18+(0.0203\times AL)+(0.281\times ACD_{pre}) \quad (6)$$

$$LHP=3.50+(0.0203\times AL)+(0.281\times ACD_{pre}) \quad (7)$$

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of selecting an intraocular lens or an optical power thereof, comprising:
   providing an eye comprising a cornea and a retina;
   determining a value of an axial length of an eye, the axial length being equal to a distance from the apex of the cornea to a surface of the retina;
   calculating, based on a mathematical relationship, a distance from the apex of the cornea to an apex or plane of the intraocular lens after an ocular surgical procedure;
   calculating an optical power of the intraocular lens suitable for providing a predetermined refractive outcome;
   wherein the mathematical relationship comprises a dependent variable that varies with a value of an independent variable, the independent variable having a base value corresponding to the determined axial length;
   wherein the mathematical relationship has a sensitivity of less than or equal to 0.5%, the sensitivity being defined as a percent variation in the dependent variable for a 1% change of the independent variable from the base value.

2. The method of claim 1, wherein the mathematical relationship has a sensitivity of less than or equal to 0.6%.

3. The method of claim 1, further comprising at least one of placing the intraocular lens behind the cornea, within the cornea, or on top of the cornea, or forming the intraocular lens from an injectable material behind the cornea, within the cornea, or on top of the cornea.

4. The method of claim 1, wherein the sensitivity is less than or equal to 0.4 percent when the method is used to calculate a position of Tecnis Z9000 intraocular lens after an ocular surgical procedure.

5. The method of claim 1, wherein the mathematical relationship includes an anterior chamber depth prior to an ocular surgical procedure.

6. The method of claim 5, wherein the distance from the apex to a plane of the intraocular lens after an ocular surgical procedure is a dependent variable $ACD_{post}$ and the mathematical relationship is:

$$ACD_{post}=C1+C2 \times AL+C3 \times ACD_{pre}+C4 \times CR,$$

where AL is an input parameter representing the axial length of the eye, $ACD_{pre}$ is an input parameter representing the anterior chamber depth prior to an ocular surgical procedure, CR is an input parameter representing a radius of curvature of the cornea, C1 is a constant with a nominal value of 4.236, C2 is a constant with a nominal value of 0.08495, C3 is a constant with a nominal value of 0.42435, and C4 is a constant with a nominal value of −0.3945, each of the constants having a value that is within plus or minus 20 percent of the nominal value thereof.

7. The method of claim 5, wherein each of the constants has a value that is within plus or minus 5 percent of the nominal value thereof.

8. The method of claim 5, wherein C1 equals 4.236, C2 equals 0.08495, C3 equals 0.42435, and C4 equals −0.3945.

9. The method of claim 5, wherein the calculated position is a calculated distance between the cornea and a lens haptic plane of an intraocular lens and the mathematical relationship is:

$$LHP=C1+C2 \times AL+C3 \times ACD_{pre}+C4 \times CR,$$

where LHP is the calculated distance between the cornea and a lens haptic plane, AL is an input parameter representing the axial length of the eye, $ACD_{pre}$ is an input parameter representing the anterior chamber depth prior to an ocular surgical procedure, CR is an input parameter representing a radius of curvature of the cornea, C1 is a constant with a nominal value of 4.556, C2 is a constant with a nominal value of 0.08495, C3 is a constant with a nominal value of 0.42435, and C4 is a constant with a nominal value of −0.3945, each of the constants having a value that is within plus or minus 20 percent of the nominal value thereof.

10. The method of claim 5, wherein the calculated position is a calculated anterior chamber depth, $ACD_{post}$, and the mathematical relationship is:

$$ACD_{post}=C1+C2 \times AL+C3 \times ACD_{pre},$$

where AL is an input parameter representing the axial length of the eye, $ACD_{pre}$ is an input parameter representing the anterior chamber depth prior to an ocular surgical procedure, C1 is a constant with a nominal value of 3.18, C2 is a constant with a nominal value of 0.0203, and C3 is a constant with a nominal value of 0.281, each of the constants having a value that is within plus or minus 20 percent of the nominal value thereof.

11. The method of claim 5, wherein the calculated position is a calculated distance between the cornea and a lens haptic plane of an intraocular lens and the mathematical relationship is:

$$LHP=C1+C2 \times AL+C3 \times ACD_{pre},$$

where LHP is the calculated distance between the cornea and a lens haptic plane, AL is an input parameter representing the axial length of the eye, $ACD_{pre}$ is an input parameter representing the anterior chamber depth prior to an ocular surgical procedure, C1 is a constant with a nominal value of 3.50, C2 is a constant with a nominal value of 0.0203, and C3 is a constant with a nominal value of 0.281, each of the constants having a value that is within plus or minus 20 percent of the nominal value thereof.

12. The method of claim 1, wherein the mathematical relationship includes a radius of curvature of the cornea.

13. The method of claim 1, wherein the mathematical relationship is independent of a radius of curvature of the cornea.

14. The method of claim 13, wherein calculating an optical power of the intraocular lens comprises calculating an optical power of an intraocular lens for use with a subject that has previously undergone a corneal refractive procedure.

15. The method of claim 1, wherein the mathematical relationship includes measured or calculated parameters of the eye that are multiplied together.

* * * * *